US006364905B1

(12) United States Patent
Simpson et al.

(10) Patent No.: US 6,364,905 B1
(45) Date of Patent: Apr. 2, 2002

(54) TRI-COMPOSITE, FULL ROOT, STENTLESS VALVE

(75) Inventors: Charles L. Simpson, Austin; Brian K. McIlroy, Georgetown; Lisa G. O'Connor, Austin, all of TX (US); Ivan Casagrande, Minas Gerais (BR); Stephen Westaby, Woodstock (GB)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/360,423

(22) Filed: Jul. 23, 1999

Related U.S. Application Data

(60) Provisional application No. 60/117,375, filed on Jan. 27, 1999.

(51) Int. Cl.$^7$ ................................................ A61F 2/24
(52) U.S. Cl. .................... 623/2.13; 623/2.15; 623/2.16; 623/910
(58) Field of Search ............................. 623/2.13, 2.14, 623/2.15, 2.16, 910

(56) References Cited

U.S. PATENT DOCUMENTS

| 4,666,442 A | | 5/1987 | Arru et al. ....................... 623/2 |
|---|---|---|---|
| 4,979,956 A | * | 12/1990 | Silvestrini ................ 623/13.11 |
| 5,147,514 A | | 9/1992 | Mechanic .............. 204/157.68 |
| 5,156,621 A | | 10/1992 | Navia et al. .................... 623/2 |
| 5,336,258 A | | 8/1994 | Quintero et al. ............... 623/2 |
| 5,449,384 A | * | 9/1995 | Johnson ..................... 623/2.13 |
| 5,861,028 A | | 1/1999 | Angell ........................... 623/2 |
| 5,928,281 A | * | 7/1999 | Huynh et al. .............. 623/2.14 |
| 5,935,163 A | * | 8/1999 | Gabbay ..................... 623/2.13 |
| 6,074,419 A | * | 6/2000 | Healy et al. ............... 623/2.14 |

FOREIGN PATENT DOCUMENTS

| WO | WO97/25004 | 7/1997 |
|---|---|---|
| WO | WO97/249989 | 7/1997 |
| WO | WO98/29146 | 7/1998 |

OTHER PUBLICATIONS

Information Brochure: Considerations for the Clinical Use of the CarboMedics "Top Hat" Supra–Annular Aortic Valve.
Information Brochure: The Inside Story on Safety.
Information Brochure: 16MM and 18MM Prosthetic Heart Valves.
Information Brochure: Solutions for Life—Sulzer Carbomedics Product Catalog.

* cited by examiner

*Primary Examiner*—Corrine McDermott
*Assistant Examiner*—Choon P. Koh
(74) *Attorney, Agent, or Firm*—Timothy L. Scott

(57) ABSTRACT

A bioprosthetic heart valve is disclosed. In a first aspect of the invention, a prosthetic heart valve comprises three mammalian heart valve leaflets, each valve leaflet including a full root length of tissue, the valve leaflets being affixed to one another to define a fluid flow passage, the fluid flow through which may be governed by the valve leaflets. In a second aspect the heart valve comprises a plurality of heart valve leaflets affixed to one another to define a fluid flow passage, the fluid flow through which may be governed by the valve leaflets; and a permanent trimming guide on at least one of the plurality of valve leaflets. In yet a third aspect of the invention, a bioprosthetic heart valve comprises a plurality of assembled parts, wherein the assembled parts are sutured together by hidden and locking stitches.

37 Claims, 5 Drawing Sheets

TRI-COMPOSITE, FULL ROOT, STENTLESS VALVE

BACKGROUND OF THE INVENTION

Pursuant to 35 U.S.C. §119(e), this application claims the earlier effective filing date of Provisional Application Serial No. 60/117,375, entitled "Tri-Composite Full Root Stentless Valve," filed Jan. 27, 1999, in the name of Charles L. Simpson, Brian K. McIlroy, Stephen Westaby, and Ivan Casagrande.

FIELD OF THE INVENTION

This invention pertains generally to a bioprosthetic heart valve and, more particularly, a tri-composite, full root, stentless valve.

DESCRIPTION OF THE RELATED ART

Prosthetic heart valves are frequently used to replace failed heart valves. There are two broad categories of prosthetic heart valves: mechanical and tissue. Mechanical heart valves are quite durable, but require anti-coagulation therapy to prevent blood clotting in the patients receiving them. Tissue valves, or "bioprosthetic" heart valves, are therefore commonly preferred over mechanical valves.

Each of the known types of bioprosthetic heart valve also has its peculiar limitations. For instance, homografts from donor human hearts are difficult to obtain in exact sizes, cannot be sterilized, and require extensive tests to determine the risks of transmitting diseases and of donor tissue incompatibility. Xenografts, or bioprostheses procured from animals other than humans, provide an acceptable alternative to homografts because they can be provided in acceptable quantities and in a variety of sizes, and they can be sterilized and tested for disease. Thus, xenografts are generally preferred over homografts. Among xenografts, porcine is generally preferred, although other types of xenografts, such as bovine, ostrich, and kangaroo, are known.

Animal valves are commonly trimmed by cutting away the aortic wall between the leaflets and leaving only the tissue to which leaflets are attached. To support the remaining structure, animal valves are usually supported by metallic or plastic "stents." A stent is a structural support, or frame, for the tissue that actually forms the valve. Typically, the valve tissue is stitched to cloth covering the stent(s). The cloth covers and is attached to the stent principally to provide a basis for attaching the tissue. The stent is often augmented by a sewing ring usually attached to the exterior of the prosthesis to aid in surgical attachment into the patient's aorta. The sewing ring and/or stent occupies space in the patient's annulus, thereby reducing the orifice area of the valve and consequently increasing turbulence and the pressure gradient. In addition, the stent tends to be somewhat rigid, requiring the leaflets to absorb much of the stress during valve closure.

Stentless tissue valves have relatively superior hemodynamics, i.e., fluid flow characteristics of blood through the valve, and potential for improved durability. A variety of stentless valves are generally known, including those disclosed in the following patents: U.S. Letters Pat. No. 5,336,258, entitled "Stentless Heart Valve and Holder," issued Aug. 9, 1994, to Baxter International, Inc. as the assignee of the inventors Quintero, et al.; U.S. Letters Pat. No. 5,156,621, entitled "Stentless Bioprosthetic Cardiac Valve," issued Oct. 20, 1992, to the inventors Navia, et al.; and U.S. Letters Pat. No. 4,666,442, entitled "Cardiac Valve Prosthesis with Valve Flaps of Biological Tissue," issued May 19, 1987, to Sorin Biomedia S.p.A. as the assignee of the inventors Arru et al.

However, each of these valves suffers some drawbacks. For instance, each porcine aortic valve comprises a single xenograft, i.e., the entire valve is extracted whole from the donor and implanted into the recipient. Thus, they are of uneven dimension. This is particularly problematical in that the valve leaflets will typically be of different sizes. Although this is natural in porcine valves, it does have some undesirable ramifications on operations and function.

SUMMARY OF THE INVENTION

A bioprosthetic heart valve is disclosed. In a first aspect of the invention, a prosthetic heart valve comprises three mammalian heart valve leaflets, each valve leaflet including a full root length of tissue, the valve leaflets being affixed to one another to define a fluid flow passage, the fluid flow through which may be governed by the valve leaflets. In a second aspect the heart valve comprises a plurality of heart valve leaflets affixed to one another to define a fluid flow passage, the fluid flow through which may be governed by the valve leaflets; and a trimming guide on at least one of the plurality of valve leaflets. In yet a third aspect of the invention, a bioprosthetic heart valve comprises a plurality of assembled parts, wherein the assembled parts are sutured together by hidden and locked stitching.

BRIEF DESCRIPTION OF THE DRAWINGS

The invention may be understood by reference to the following description taken in conjunction with the accompanying drawings, in which like reference numerals identify like elements, and in which:

FIG. 6A illustrates an alternative method for trimming the valve sections to remove muscle tissue.

Figure 1:
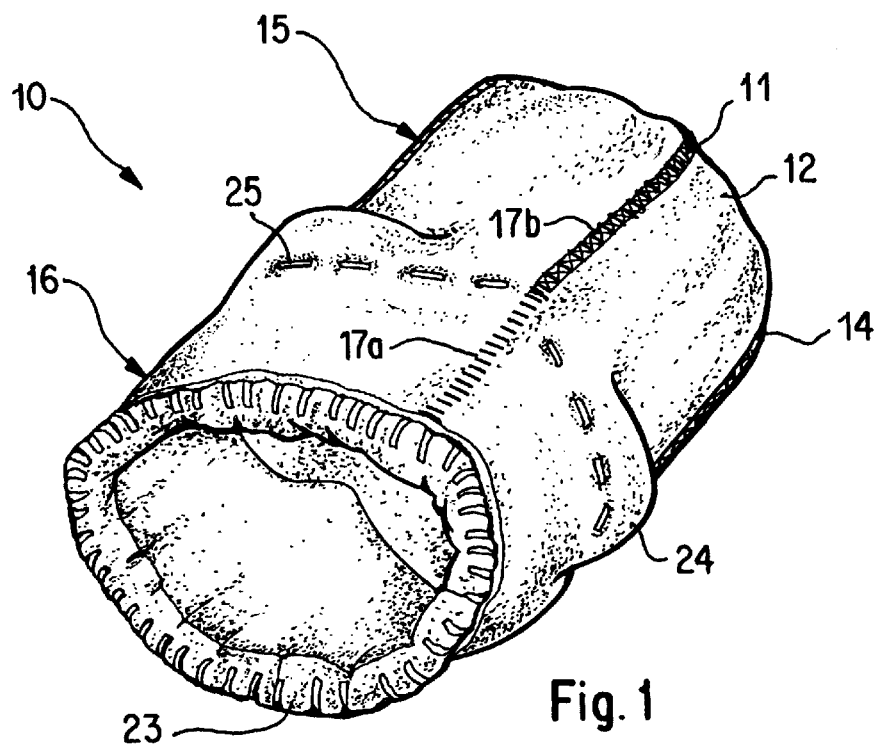
FIG. 1 is a perspective view of one particular embodiment of a bioprosthetic heart valve constructed in accordance with several aspects of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

FIGS. 1–5 illustrate one particular embodiment of a bioprosthetic heart valve manifesting several aspects of the present invention. More particularly, these drawings illustrate a full root, stentless heart valve 10 that is prepared from rectangularly-shaped portions 12 of non-human animal heart valve tissue. Preferably, the animal tissue is made from porcine or bovine tissue. The portions are elongate strips of the original valve that includes intact leaflet material. These portions may be trimmed to remove extraneous muscle tissue. The void resultant from muscle trimming can be filled by the adjacent leaflet. Unlike prior heart valves, these sections may be subjected to a photochemical fixation procedure such as described in U.S. Pat. No. 5,147,514, incorporated herein by reference. Alternatively, gluteraldehyde fixation may also be used. In addition, the full root heart valve that has been excised from an animal is treated either before or after the section with a leaflet has been cut away. If the full heart valve is treated prior to being cut, then the sections may be reassembled with any leaflet section, which provides the desired matching of leaflets.

Figure 2:
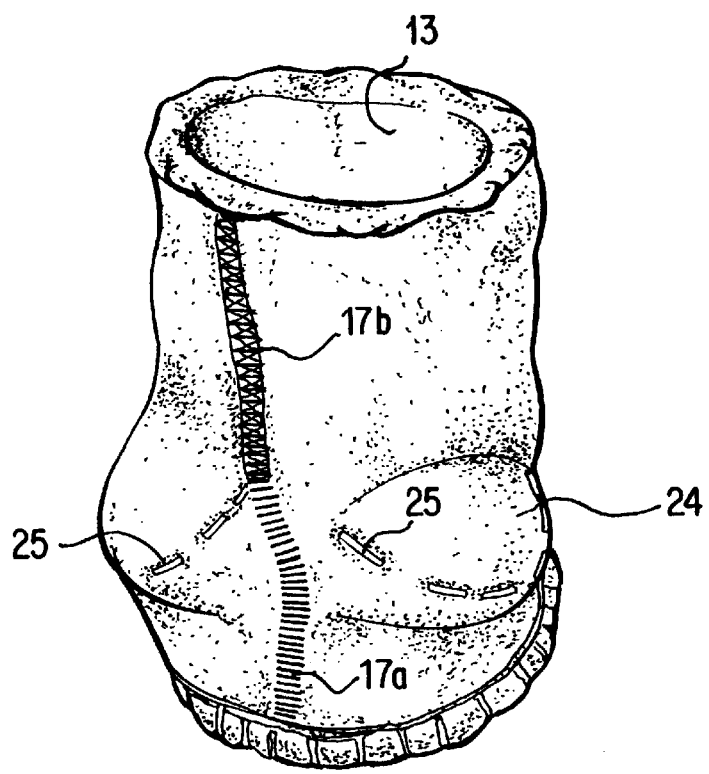
FIG. 2 is a second perspective view of the heart valve shown in FIG. 1.
Figure 3:
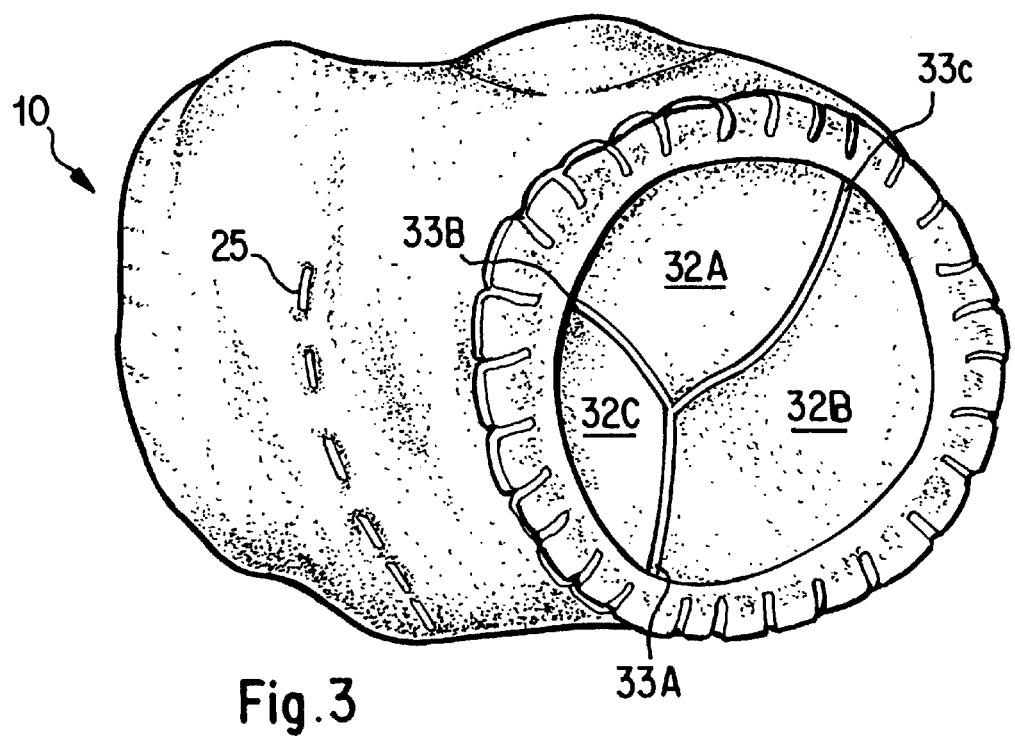
FIG. 3 is a third perspective of the heart valve shown in FIG. 1, wherein this view shows the valve leaflets.

FIGS. 1–3 illustrate the bioprosthetic heart valve 10 in various elevational views. The tri-composite heart valve 10 is formed from three pieces of pre-treated leaflet sections 12, which have been combined through use of sutures 11. As mentioned earlier, the sections 12 have been excised from non-human heart tissue, preferably porcine aortic valve tissue. The valve 10, which may be seen to have a generally tubular shape, includes an external surface 14 and an inner surface 13 as shown in FIG. 2. In use, the blood flows through the valve 10 from the inflow end 16 toward the outflow end 15.

Figure 6:
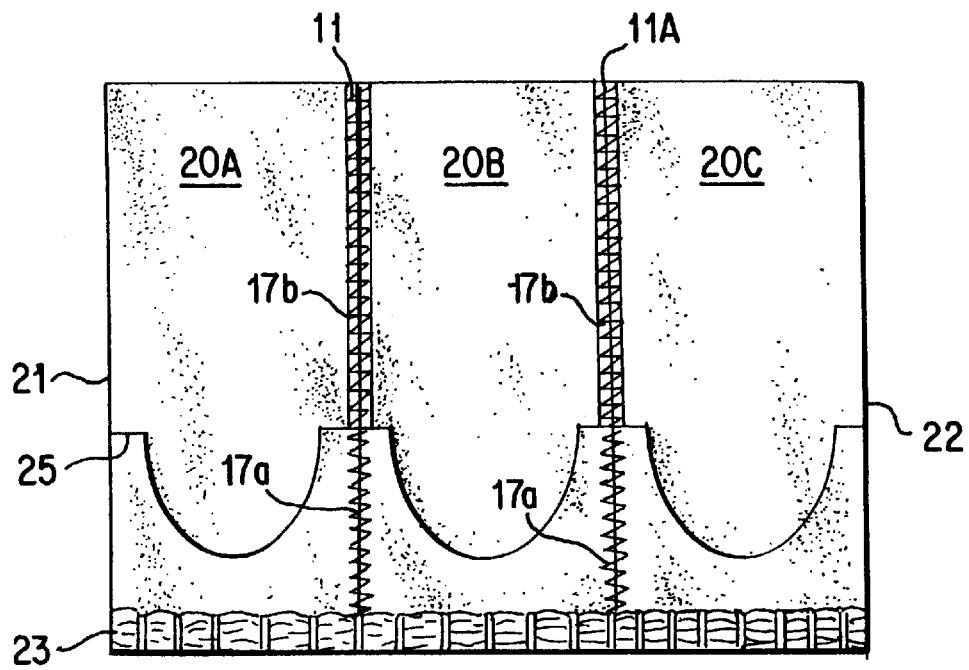
FIG. 6 illustrates three leaflets that have been partially sutured together during the assembly of the heart valve of FIG. 1.

As shown in FIGS. 6 and 6A, the three sections 20A, 20B and 20C that make up the final valve are stitched together on the edges using sutures 11, which form a suture line 11A. Each group of sutures 11 includes two groups: hidden sutures 17a and locking sutures 17b. The sutures 17a are hidden, i.e., they do not pierce the interior surface 13 of the valve 10. This construction technique minimizes the possibility of contact with the leaflet. The group 17a is stitched with a thread having a first color using any suitable technique known to the art. The hidden sutures 17a extend from the edge of the inflow end 16 to a point at which the free margin or edge of the leaflet intersects the interior surface 13 of the valve 10. The locking sutures 17b are so-called because they resist unraveling even when cut, e.g., when trimmed for implantation. The second group 17b is stitched with a thread having a second color different from first color. The second group 17b is stitched using the technique of FIGS. 8A–8E, which is discussed more fully below. This group extends from the edge of the outflow end 15 to where the first group 17a of sutures 11 ends.

The second group 17b of the sutures 11 serves an important purpose furthered by some of its principle characteristics. Because it uses the stitching technique illustrated in FIGS. 8A–8E, it will not unravel when cut by the surgeon while trimming the full root during implantation. Because it is stitched in a color, preferably a distinct one, different from that of the first group 17a of sutures 11, and extends to the end of the sutures 17a, it demarks the area of the valve sections 20A–C that may be trimmed during implantation. Thus, the second group 17b of sutures 11 functions as trimming guide. FIG. 6A illustrates an alternative method of trimming valve sections 20A–C to remove muscle tissue and stitching to maintain a cylindrical shape.

Figure 7:
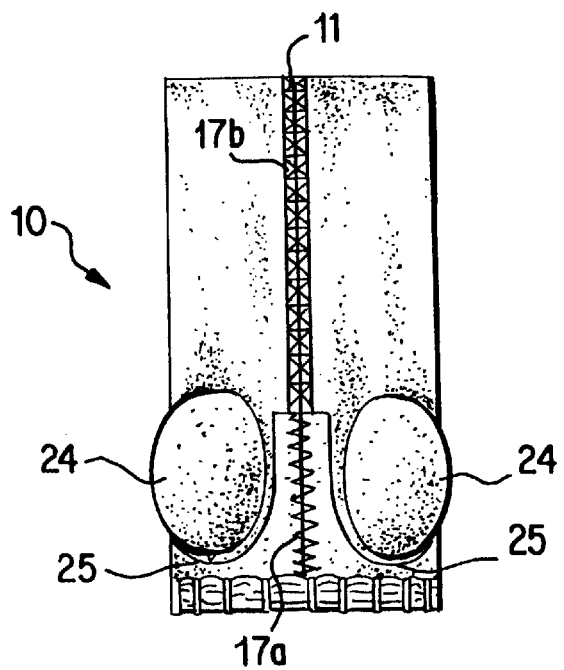
FIG. 7 is a side view of three leaflets after having been fully sutured together, with the suture lines being shown.

The outside edges 21, 22 of the partially formed valve in FIG. 6 are then stitched with sutures such as the suture lines 11A to form the elongate body shown in FIG. 7. Each section 20A, 20B and 20C may include a pericardial tissue covering on the inflow portion of each section. The pericardial covering 23, which may be stitched into place using known techniques, may serve as a sewing ring. In the particular embodiment illustrated, the pericardial covering 23 is stitched using a blanket stitch such that the individual sutures are "hidden," i.e., do not pierce the interior surface of the pericardial covering 23. The blanket stitch may also serve as a suturing guide for the surgeon. The fully assembled valve 10 may include a sinus 24 in each section of the tri-composite valve 10, although the invention is not so limited. FIG. 7 shows a suture trim guide 25 for the benefit of the surgeon.

Figure 9:
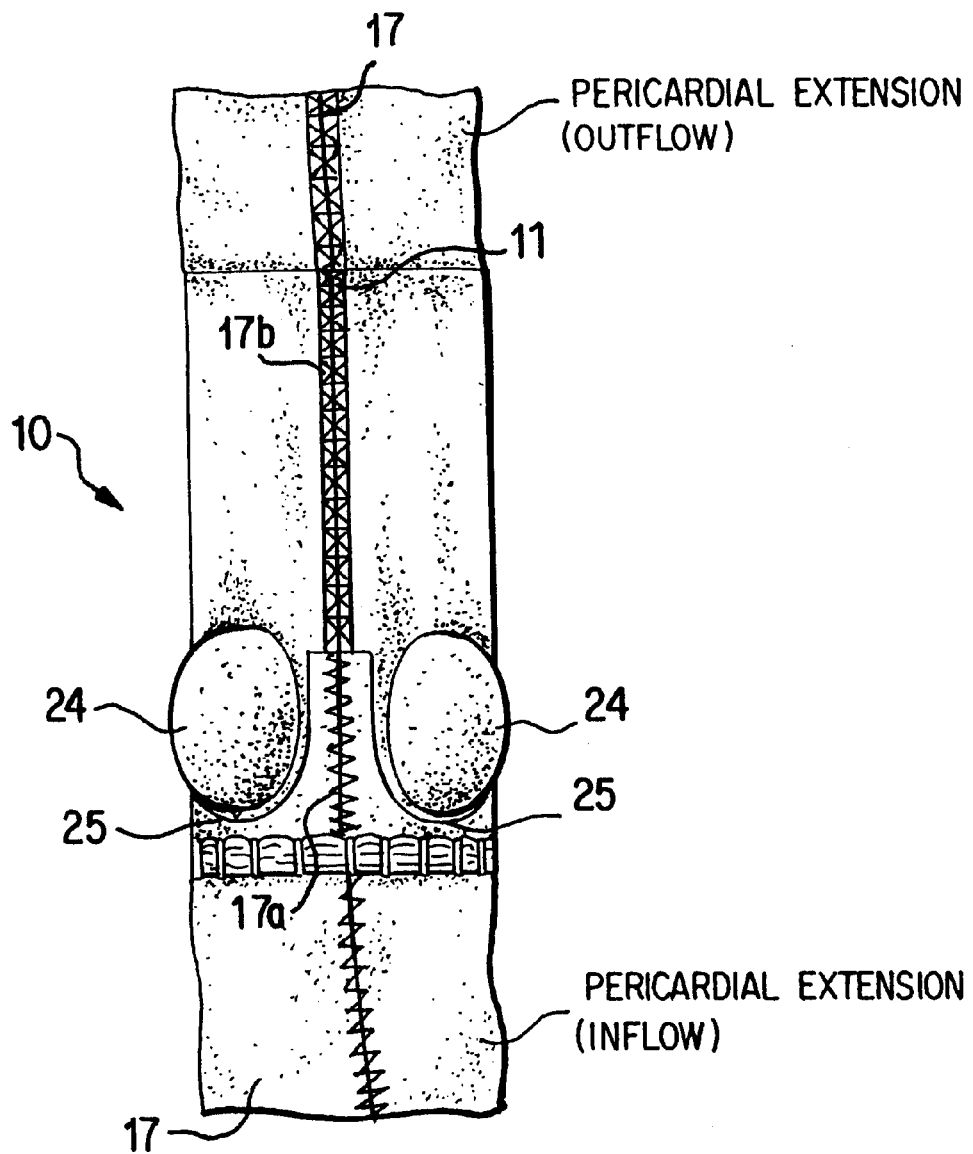
FIG. 9 illustrates pericardial extensions on the inflow and outflow ends.

FIG. 9 shows pericardial extensions on the inflow end and the outflow end of the valve 10. The extensions can be trimmed by the surgeon to facilitate valve implantation. The extensions may be constructed using locked and hidden sutures such as the sutures 17a, 17b, discussed above.

Figure 4:
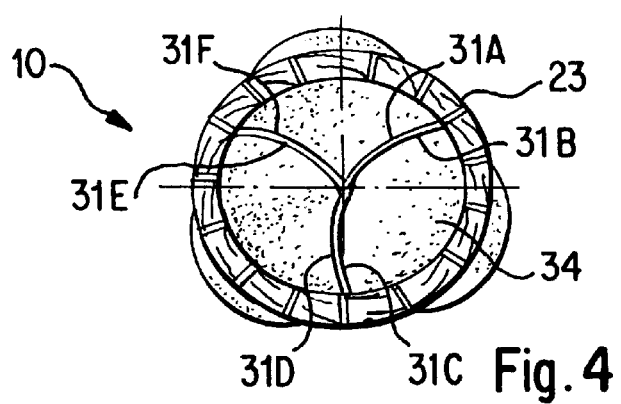
FIG. 4 is a plan view of the heart valve in FIG. 1 from the inflow side opposite the root.
Figure 5:
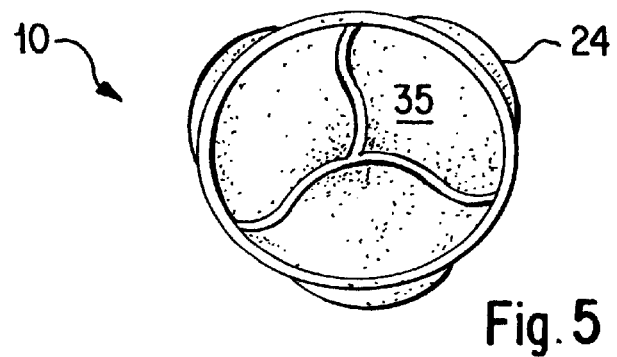
FIG. 5 is a plan view of the heart valve of FIG. 1 from the outflow side of the root.

The leaflets include cusps 32A, 32B and 32C which come together in the assembled valve 10 at adjacent edges 31A/31B, 31C/31D and 31E/31F to form coaptation zones 33A, 33B and 33C, as depicted in FIGS. 3–5. The leaflet sections 20A–20C may be pre-selected to match the leaflets and limit any gaps in the commissures to thereby optimize operation of the leaflets during use. In FIG. 4, which is a view of the inflow end 16 of a valve 10, inflow sides 35 of the leaflets are shown. Again, the flow of blood during use is away from the viewer in FIG. 4. In FIG. 5, the flow is toward the viewer. In FIG. 5, the outflow sides 35 of the leaflets are shown.

The size of the heart valve 10 may be varied. In general, the heart valve 10 will have an outside diameter of from about 17 to about 33 millimeters. The size of the valve is typically based on the size of the leaflet sections procured from the donor animal. The size selected for implantation will depend on the requirements of the patient. The heart valves that are excised from the donor animals should preferably be free of anatomical abnormalities and be free of holes in the leaflets or cusps. The leaflet sections may be removed from the donor animals, and the sections cut from the removed animal heart valves, using known techniques.

Figure 8A:
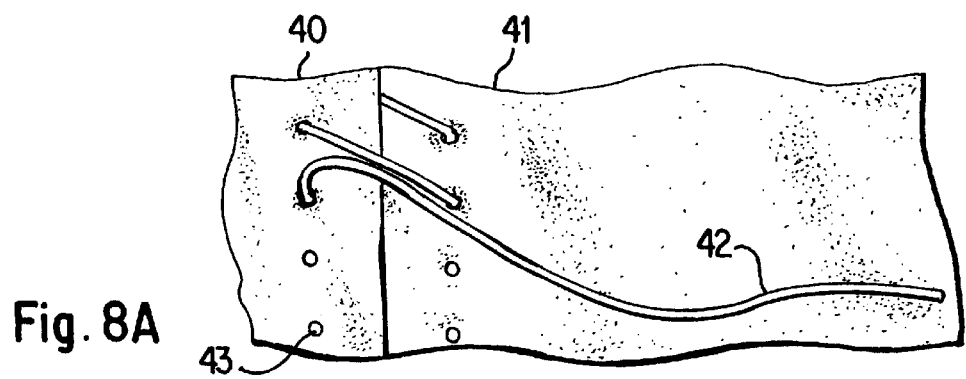
FIGS. 8A–8E illustrate a suture method which may be used in the construction of a heart valve and which advantageously does not unravel when cut.
Figure 8B:
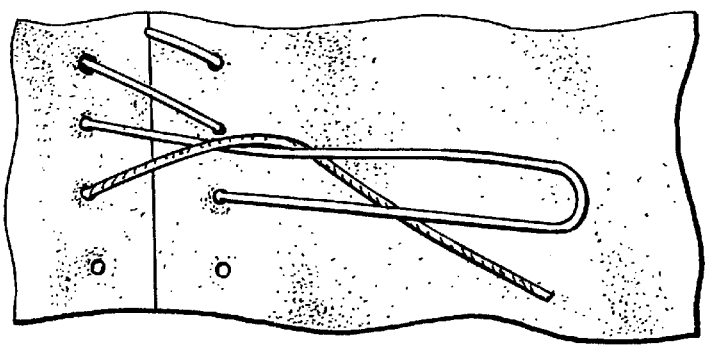
Figure 8C:
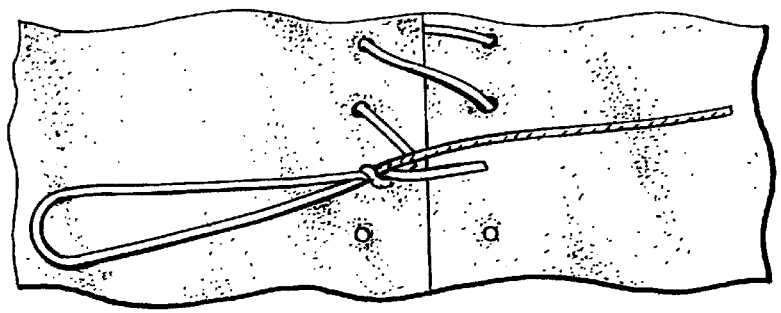
Figure 8D:
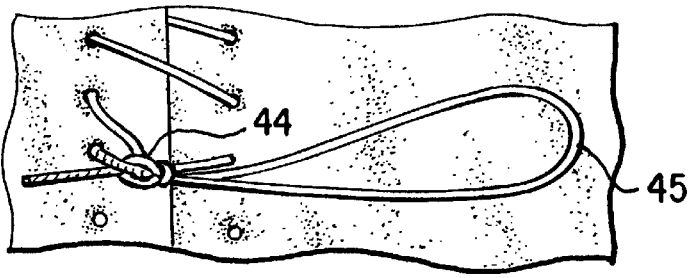
Figure 8E:
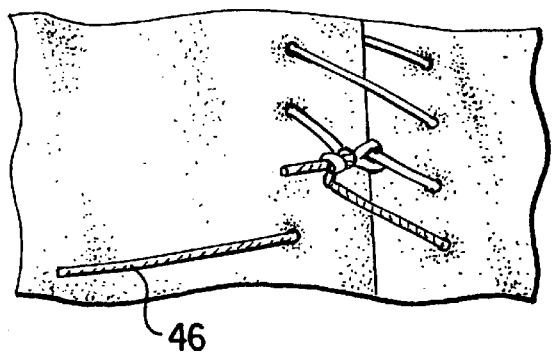

FIGS. 8A–8E depict the stitching sequence used to make sutures that do not unravel when cut. The flaps 40, 41 may be two leaflet sections, such as 20A, 20B or 20C. The suture material is threaded at points 43 as shown in FIGS. 8A–8B. A square knot 44 is then made every fourth stitch. The end of the suture material 46 is then used to make additional stitches and square knots. The shading of end 46 is for purposes of illustration only. After completing the square knot 44, the excess suture material 45 (the loop) may be trimmed. In one embodiment, the spacing of the points 43 are every 1 millimeter. The suture material may be, for example, a braided polyester suture material. In one embodiment, the color of the suture material is green, although the color of the suture material is not material to the practice of this invention.

The heart valve 10 may be implanted into a patient using known techniques. During implantation, the valve 10 may be trimmed as appropriate for the circumstances. The trimming guide 25 and the first group 17a of the sutures 11 should not be trimmed. The trimming guide 25 demarcates the areas of the valve 10 that may be trimmed without impairing the valve 10's function after implantation. Trimming is acceptable from the trimming guide 25 to the outflow end, which includes 17b. The pericardial covering 23 contains a stitch, which facilitates surgeon suture placement by indicating where sutures can be placed without damaging the leaflets.

As mentioned, the tissue of the valve 10, in the particular embodiment illustrated, may be either photo-oxidized or treated with gluteraldehyde. A photo-oxidation fixation treatment in the practice of the present invention efficiently and effectively cross-links and stabilizes various proteinaceous materials including, but not limited to, collagen, collagen fibrils and collagen matrices. The term proteinaceous material as used herein includes both proteins such as collagen and protein-containing materials such as tissues. The valve 10 may be fabricated from tissue treated with a dye-mediated photo-oxidation process. One particular dye-mediated photo-oxidation process suitable for this purpose is known to the art as PhotoFix®, various aspects of suitable processes are further disclosed in U.S. Letters Pat. No. 5,147,514, entitled "Process for Cross-Linking Collagenase Material and Resulting Product," issued Sep. 15, 1992, to the University of North Carolina as assignee of the named inventor G. L. Mehanic; and in Moore, M. A., "Pericardial Tissue Stabilized by Dye-Mediated Photooxidation: A Review Article," *J. Hrt. Valve Dis.* 1996; 6:521–26. Dye-mediated photo-oxidation treated tissue has been found to be stable toward chemical, enzymatic, and in vivo degradation while maintaining physical properties of natural tissue. This material has also been shown to support endothelial cell growth, is biocompatible, and relatively nonimmunogenic. In addition, bioprosthetic heart valves prepared from photo-oxidized tissue have demonstrated in vivo resistance to calcification.

The particular embodiment of FIGS. 1–7, i.e., the prosthetic heart valve 10, manifests several separate aspects of the present invention. Three of these aspects are discussed in further detail below. These aspects may be practiced severally, or jointly in various permutations. More particularly, the three aspects discussed below are a tri-composite, stentless, prosthetic heart valve including a full root length of tissue, a prosthetic heart valve including a trimming guide, and a prosthetic heart valve employing hidden sutures in conjunction with locking sutures.

A first aspect of the present invention is a tri-composite, stentless, prosthetic heart valve including a full root length of tissue. A "full root length" of tissue, as used herein, means a graft including a length of porcine aortic wall including the sinuses of valsalva. Thus, the valve leaflets 20A–C in the embodiment illustrated include not only the edges and cusps of the valve leaflets, but also a portion of the donor's aortic outflow tract.

More particularly, this first aspect is a prosthetic heart valve, e.g., the valve 10, comprising three mammalian heart valve leaflets, e.g., the leaflets 20A–C. Each valve leaflet includes a full root length of tissue, the valve leaflets being affixed to one another to define a fluid flow passage, the fluid flow through which may be governed by the valve leaflets. As will be appreciated by those skilled in the art having the benefit of this disclosure, the leaflets will not control the fluid flow, inasmuch as they merely prevent regurgitation of fluid pumped therethrough. Thus, the valve leaflets merely govern fluid flow by permitting fluid flow in one direction while preventing regurgitation.

In accordance with this first aspect of the invention, the valve leaflets may be xenografts, homografts, or a combination of the two. Embodiments employing both xenografts and homografts will probably rarely be encountered, however. Again, xenograft types may be mixed and matched, but it is anticipated this will rarely occur. The valve leaflets 20A–C of the valve 10 in FIGS. 1–7 are porcine xenografts.

The valve leaflets may be either aortic or pulmonary. The valve leaflets 20A–C in the valve 10 of FIGS. 1–7 are aortic, and the full root length of tissue 1–3 cm from below an annulus defined by the valve leaflets 20A–C in the fluid flow passage to 1–3 cm above the sinotubular junction of the aorta.

The tissue of the valve, in accordance with this particular aspect of the invention, may be fixed using any suitable technique known to the art. Two suitable techniques are gluteraldehyde fixation and photofixation, although the invention, in this first aspect, is not so limited. Other techniques may become apparent to those skilled in the art having the benefit of this disclosure.

The valve leaflets may be affixed to one another using any suitable technique known to the art in accordance with this first aspect. Exemplary techniques include adhesion, fusion, and stitching, although the invention is not so limited. As with fixation, other suitable affixation techniques may become apparent to those skilled in the art having the benefit of this disclosure. The particular embodiment illustrated in FIGS. 1–7, i.e., the valve 10, stitches the valve leaflets 20A–C together using a hidden suture 17a and a locking suture 17b in accordance with the third aspect of the invention discussed further below. Further, as discussed above, this locking suture 17b is stitched in a manner such that the suture will not unravel when cut or trimmed.

A prosthetic heart valve may, in accordance with this first aspect of the invention, employ a permanent trimming guide in accordance with the second aspect of the invention discussed immediately below. The valve 10 in FIGS. 1–7 includes several trimming guides, notably the trimming guide 25 and the colored sutures 17b. However, the invention is not so limited and alternative embodiments might, in accordance with this first aspect of the invention, omit trimming guides altogether.

The second aspect of the present invention is a prosthetic heart valve including a permanent trimming guide. As used herein, the term "permanent" shall mean sufficiently durable to persist at least until after the prosthetic heart valve 10 is implanted. The term, as used herein, does not imply permanence in the sense that the trimming guide may never be removed or wear away. It is sufficient for purposes of the invention that the trimming guide persist until after implantation. Thus, the trimming guide may be implemented in many variations. Such variations include, but are not limited to a permanent suture, a biodegradable suture, a dissolvable suture, a resorbable suture, a tattooed marking, and a drawn marking. Still other variations may become apparent to those skilled in the art having the benefit of this disclosure.

More particularly, this second aspect of the invention is a prosthetic heart valve, e.g., the valve 10, comprising a plurality of heart valve leaflets, e.g., the valve leaflets 20A–C, and a trimming guide, e.g., the colored sutures 17b and/or the trimming guide 25. The valve leaflets are affixed to one another to define a fluid flow passage through which fluid flow may be governed by the valve leaflets. The permanent trimming guide is on at least one of the plurality of valve leaflets.

The trimming guide, in this aspect of the invention, may take many guises. The trimming guide may be a permanent suture, a biodegradable suture, a dissolvable suture, a resorbable suture, a tattooed marking, and a drawn marking, although this is not an exhaustive listing. For instance, both the trimming guide 25 and the colored sutures 17b in FIGS. 1–7 both constitute trimming guides. They may be used jointly, as in the valve 10, or may be used severally in embodiments not illustrated. Thus, the trimming guide may indicate a portion of a full root length of tissue that may be trimmed or the location of the edges and cusp of one of the valve leaflets. The trimming guide may also be a suture stitched from thread of a first color indicating a trimming area and thread of a second color indicating a non-trimming area, or may include a suture that will not unravel when cut. The trimming guide may include hidden stitching where the suture does not penetrate the interior surface of the valve.

The variations in the form and function of the trimming guide may be practiced in many permutations. Thus, the trimming guide 25 and the colored sutures 17b are, by way of example and illustration, but two means for indicating where a bioprosthetic valve may be trimmed. Other, equivalent structures performing the identical function may become apparent to those in the art having the benefit of this disclosure. Each of these permutations and variations is considered within the scope and spirit of the invention.

A third aspect of the present invention is a prosthetic heart valve employing hidden and locking sutures. Hidden sutures do not pierce the interior surface of the valve and minimize the possibility of contacting the valve leaflets. This construction reduces the possibility of abrasion damage to the leaflets. Locking sutures will not unravel when cut or trimmed. Like the other aspects of the present invention, this aspect admits wide variation. The hidden stitching sutures 17a may stitch a pericardium covering lip 23, to a valve section, e.g., sections 20A–C or two valve leaflets, e.g., leaflets 20A–C, together. The locking stitches 17b may include square knots, or some stitching that will not unravel when cut. The hidden stitching 17a and locking stitching 17b may include thread of a first color indicating a trimming area and thread of a second color indicating a non-trimming area. The hidden sutures 17a may be constructed as locking sutures and be located on the outflow and/or the inflow end of the valve. This technique advantageously provides an interior blood flow surface free of synthetic material (i.e., suture) while still allowing the suture to be cut or trimmed without unraveling.

The present invention, in its various aspects, affords numerous advantages over the known art, particularly when the aspects are practiced in conjunction. For example, because the heart valve of this invention can be constructed after chemical fixation of the leaflet sections that have been harvested from a porcine or bovine source. The pretreatment of the tissue in accordance with this invention allows the leaflets to be selected to optimize the fit of the leaflets resulting in matched leaflets.

Still other advantages will become apparent to those skilled in the art having the benefit of this disclosure. For instance, stentless valves provide better flow characteristics and maximized flow area during use. Furthermore, the full length suture line of this invention may be trimmed without unraveling. Moreover, a tri-composite valve eliminates the coronary ostia and allows for more precise and favorable attachment of the patients coronaries and eliminates the muscle shelf. Also, elimination of cloth as part of the valve (e.g., a sewing cuff) increases the biocompatability of the device in relation to tissue response and inflammation. Still further, elimination of cloth is believed to improve durability by lessening the abrasion to which the leaflets may be subjected. What is more, a full root valve has more implanting options than a sub-coronary design.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A prosthetic composite heart valve, comprising three mammalian heart valve leaflet sections, each leaflet section including a full root length of tissue and a valve leaflet and being devoid of coronary ostia, the leaflet sections being affixed to one another to define a fluid flow passage, the fluid flow through which may be governed by the valve leaflets.

2. The prosthetic heart valve of claim 1, wherein the leaflet sections are selected from the group comprising xenografts and homografts.

3. The prosthetic heart valve of claim 2, wherein at least one of the valve leaflets is a xenograft comprising a porcine valve leaflet.

4. The prosthetic heart valve of claim 1, wherein at least one of the valve leaflets is aortic.

5. The prosthetic heart valve of claim 1, wherein at least one of the valve leaflets is pulmonary.

6. The prosthetic heart valve of claim 1, wherein at least one of the valve leaflets is a non-coronary, xenograph valve leaflet.

7. The prosthetic heart valve of claim 1, wherein at least one of the valve leaflets has been trimmed to exclude extraneous muscle tissue resulting in a void in said leaflet that has been trimmed.

8. The prosthetic heart valve of claim 7, wherein the void resulting from muscle trimming is filled by the adjacent leaflet.

9. The prosthetic heart valve of claim 1, wherein the full root length of tissue for at least one valve leaflet section extends 1–3 cm below an annulus defined by the valve leaflets in the fluid flow passage and 1–3 cm above the sinotubular junction of the aorta.

10. The prosthetic heart valve of claim 1, further comprising a pericardial covering on at least one of the inflow end and the outflow end thereof.

11. The prosthetic heart valve of claim 10, wherein the pericardium covering comprises a mammalian pericardium.

12. The prosthetic heart valve of claim 11, wherein the pericardium covering is sutured to the valve using hidden stitching.

13. The prosthetic heart valve of claim 11, wherein the pericardium covering is sutured to the valve using locking stitching.

14. The prosthetic heart valve of claim 11, wherein the pericardium covering extends 1–15 cm the length of the valve.

15. The prosthetic heart valve of claim 11, wherein the pericardium covering contains a stitch which facilitates surgeon suture placement by indicating where sutures can be placed without damaging the leaflets.

16. The prosthetic heart valve of claim 1, wherein at least one of the valve leaflets is fixed using a technique selected from the group comprising gluteraldehyde fixation and photofixation.

17. The prosthetic heart valve of claim 1, wherein the valve leaflets are affixed using a technique selected from the group comprising adhesion, fusion, and stitching.

18. The prosthetic heart valve of claim 1, wherein the valve leaflets are affixed using a locking stitch.

19. The prosthetic heart valve of claim 17, wherein the valve leaflets are affixed using a suture that will not unravel.

20. A tri-composite, full root, stentless heart valve, which is devoid of coronary ostia, wherein leaflet sections that are attached to form the tri-composite have been treated by photochemical fixation prior to assembly.

21. The valve of claim 20 wherein sutures are used to attach the sections wherein the sutures are sewn such that they do not unravel when cut.

22. The valve of claim 20 including a pericardial sewing ring attached to a posterior end of the valve.

23. The valve of claim 20 wherein the leaflet sections comprise porcine or bovine tissue.

24. The valve of claim 20 wherein the valve is made of porcine tissue.

25. A prosthetic heart valve comprising a tri-composite, full root, stentless valve, which is devoid of coronary ostia, and which has been made by suturing together three pieces of animal tissue that each includes a heart valve leaflet to form a tubular structure having an external surface, an inner surface, an posterior end, a anterior end, and in which the three leaflets have cusps and edges, with the adjacent edges of the valve leaflets meeting to form commissures, wherein the pieces have been treated by photochemical fixation prior to suturing.

26. The valve of claim 25 wherein sutures are used to attach the sections wherein the sutures are sewn such that they do not unravel when cut.

27. The valve of claim 25 including a pericardial sewing ring attached to a posterior end of the valve.

28. The valve of claim 25 wherein the leaflet sections are made of porcine or bovine tissue.

29. The valve of claim 25 wherein the valve is made of porcine tissue.

30. A process for the manufacture of a prosthetic heart valve, comprising:

providing mammalian sections contain heart valve leaflets;

treating the sections using photofixation;

attaching three sections to define a tubular structure wherein the leaflets match to form commissures at adjacent edges of the leaflets;

attaching a sewing ring at a posterior end of the tubular structure;

thereby forming a full root, tri-composite, stentless heart valve devoid of coronary ostia.

31. The process of claim 30 wherein sutures are used to attach the sections wherein the sutures are sewn such that they do not unravel when cut.

32. The process of claim 30 wherein the leaflet sections are made of porcine or bovine tissue.

33. The process of claim 30 wherein the valve is made of porcine tissue.

34. A process for the replacement of a heart valve in a human, comprising: removing an existing heart valve from the human and implanting a tri-composite, full root, stentless heart valve devoid of coronary ostia wherein leaflet sections that are sutured together to form the tri-composite have been treated by photochemical fixation prior to assembly in place of the existing heart valve.

35. The process of claim 34 wherein sutures are used to attach the sections wherein the sutures are sewn such that they do not unravel when cut.

36. The process of claim 34 wherein the leaflet sections are made of porcine or bovine tissue.

37. The process of claim 34 wherein the valve is made of porcine tissue.

* * * * *